(12) United States Patent
Schaible

(10) Patent No.: US 8,718,898 B2
(45) Date of Patent: May 6, 2014

(54) STAND FOR HOLDING AT LEAST ONE MEDICAL DEVICE, HAVING ASSISTIVELY DRIVEN CASTERS

(71) Applicant: Leica Microsystems (Schweiz) AG, Heerbrugg (CH)

(72) Inventor: Joachim Schaible, Balgach (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 13/765,147

(22) Filed: Feb. 12, 2013

(65) Prior Publication Data

US 2013/0211651 A1  Aug. 15, 2013

(30) Foreign Application Priority Data

Feb. 14, 2012  (DE) .......................... 10 2012 101 136

(51) Int. Cl.
*B60T 8/32* (2006.01)
*B60T 7/12* (2006.01)

(52) U.S. Cl.
USPC ................ 701/93; 701/96; 180/19.1; 180/11; 248/124.1

(58) Field of Classification Search
USPC ................................. 180/19.1–19.3, 170–172
See application file for complete search history.

(56) References Cited

U.S. PATENT DOCUMENTS

| | | | |
|---|---|---|---|
| 8,442,738 B2 * | 5/2013 | Patmore | 701/93 |
| 2005/0080547 A1 * | 4/2005 | Scelers et al. | 701/82 |
| 2006/0064212 A1 * | 3/2006 | Thorne | 701/23 |
| 2008/0074260 A1 * | 3/2008 | Reiner | 340/568.5 |
| 2009/0001740 A1 | 1/2009 | Kofoed et al. | |
| 2009/0097957 A1 * | 4/2009 | Cramer et al. | 414/801 |
| 2010/0111660 A1 * | 5/2010 | Mathews | 414/469 |
| 2012/0024329 A1 * | 2/2012 | Ma | 135/16 |
| 2013/0008732 A1 * | 1/2013 | Richter | 180/167 |
| 2013/0099072 A1 * | 4/2013 | Butler et al. | 248/124.1 |

FOREIGN PATENT DOCUMENTS

| | | |
|---|---|---|
| DE | 8400384 | 4/1984 |
| DE | 19710950 | 1/1998 |
| DE | 19952477 | 5/2001 |
| JP | 2005143970 | 6/2005 |
| JP | 2011125580 | 6/2011 |
| WO | 2010140321 | 12/2010 |

\* cited by examiner

*Primary Examiner* — John R Olszewski
*Assistant Examiner* — Daniel Johnson
(74) *Attorney, Agent, or Firm* — Hodgson Russ LLP

(57) ABSTRACT

The invention relates to a stand (10) for holding at least one medical device (W1 to W3), which encompasses a stand foot (6) having multiple casters (16) for displacement of the stand (10). The stand (10) has a sensor unit (22) for ascertaining a displacement motion of the stand (10), a drive unit (18) for driving at least one of the casters (16), and a control unit (20) for controlling the drive unit (18). The control unit (20) applies control to the drive unit (18) in such a way that the latter assistively drives the at least one caster (16) only when the sensor unit (22) detects a displacement motion of the stand (10).

14 Claims, 1 Drawing Sheet

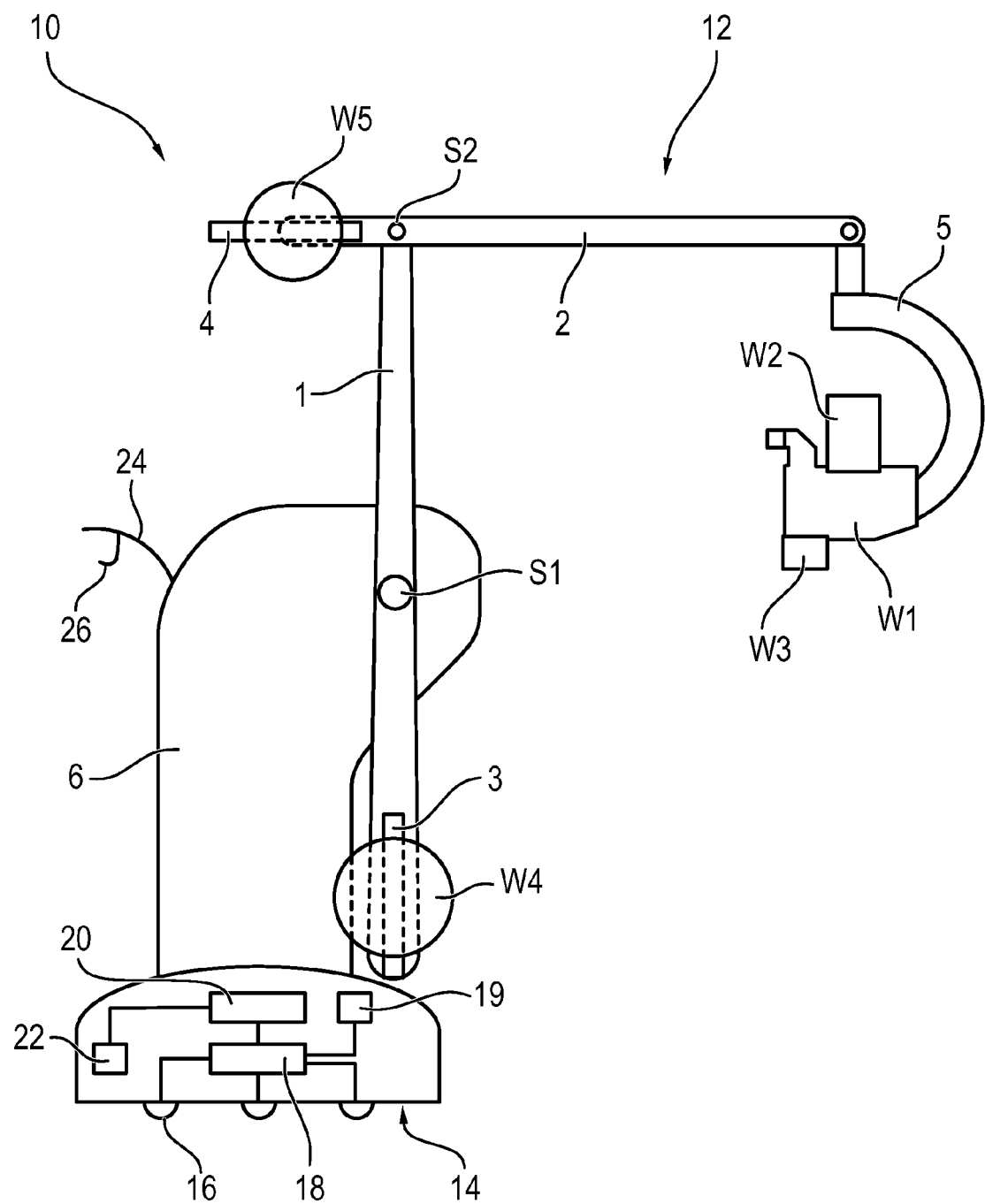

STAND FOR HOLDING AT LEAST ONE MEDICAL DEVICE, HAVING ASSISTIVELY DRIVEN CASTERS

CROSS REFERENCE TO RELATED APPLICATIONS

This application claims priority of German patent application number 10 2012 101 136.2 filed Feb. 14, 2012, the entire disclosure of which is incorporated by reference herein.

FIELD OF THE INVENTION

The invention relates to a stand for holding at least one medical device, which includes a stand foot for placing a stand on the floor, said foot having multiple casters for displacement of the stand on the floor.

BACKGROUND OF THE INVENTION

The stand is used in particular to hold microscopes, and if applicable further auxiliary apparatuses, e.g. illumination systems, in operating rooms during a surgical procedure, so that the surgeon has his or her hands free. Because a microscope of this kind is not needed for every procedure, or a specific microscope may be needed for various procedures in different operating rooms, the stands are displaced between operating rooms and possibly storage areas. It is known for this purpose that multiple casters, with which the stand can be displaced so that it does not need to be lifted, are arranged on the underside of the stand foot, i.e. that side which faces toward the floor.

As a result of the provision of an increasingly large number of modern additional devices, and the attempt to configure stands in small and compact fashion so that they require less space, modern stands are very heavy, so that displacing the stands requires a comparatively large amount of energy. In particular, the risk exists that once a stand has been set in motion, it is difficult to decelerate again manually, and in particular that a long braking distance is needed for this, so that collisions and possibly injuries and/or damage can occur.

Trolleys for medical devices that encompass electrically driven casters, so that the trolleys can be automatically displaced by actuating corresponding buttons on the trolley with no need for the operator to apply a force for that purpose, are therefore known, for example from the JANSEN MEDICARS company. A problem with such trolleys is that as a result of this electrical drive system, for example as a result of unintended pressing of a button or pressing of an incorrect button, the trolley can quickly end up being moved in an unintended direction, and injuries can thus be caused or expensive medical devices can be damaged.

SUMMARY OF THE INVENTION

The object of the invention is to describe a stand for holding at least one medical device which can easily be moved to different locations.

This object is achieved by a stand having the features described herein. Advantageous refinements of the invention are also described.

According to the present invention, the stand encompasses a sensor unit for ascertaining a displacement motion of the stand, a drive unit for driving at least one of the casters of the stand foot, and a control unit for controlling the drive unit. The control unit applies control to the drive unit in such a way that the drive unit assistively drives the at least one caster only when the sensor unit detects a displacement motion of the stand.

The result achieved thereby is that the user of the stand is assisted by the drive unit upon displacement of the stand, so that displacement is simpler; but, in contrast to a complete electrical drive system, a high level of safety is provided because the drive unit engages assistively only when the stand is being moved manually.

"Assistive driving" is to be understood in particular to mean that driving of the caster occurs only when the stand is already in motion, in particular is being moved manually.

Assistive driving of the at least one caster in order to assist displacement motion occurs, in particular, in a manner similar to a electric-power-assisted cycle, as known for example from the document DE 197 10 950 C2.

A "displacement motion" of the stand represents a movement of the stand on the floor from a first location to a second location. The displacement motion is, in particular, not a motion of carrier units of the stand.

Arranged on the stand foot is, in particular, a carrier unit on which the medical device is in turn mountable. The carrier unit is connected in particular articulatedly to the stand foot, so that the medical device mounted on said unit can be brought into a desired position with no need to move the stand foot for that purpose. The carrier unit encompasses in particular two carriers that are in turn connected articulatedly to one another, so that the greatest possible motion spectrum is possible.

The carrier unit preferably has a holding unit on which the medical device is mounted. A microscope is preferably mounted on the holding unit as a medical device. In addition to the microscope, further auxiliary apparatuses, for example an illumination system, can also be mounted on the holding unit or directly on the microscope.

It is furthermore advantageous if the drive unit assistively drives at least two casters of the stand foot, preferably all casters of the stand foot, when the sensor unit detects a displacement motion. The result achieved thereby is that the stand foot is assistively moved in uniform fashion.

The drive unit can encompass in particular an electric motor, preferably a direct-current motor. A simple, economical configuration is thereby achieved.

It is furthermore advantageous if the stand encompasses an energy storage unit for storing electrical energy in order to supply the drive unit with energy. This has the advantage that the stand does not need to be connected to an electrical grid for displacement. The energy storage unit preferably encompasses a rechargeable battery, so that the energy storage unit is rechargeable. The stand has, in particular, an interface for charging said rechargeable battery, through which the latter can be connected to an electrical grid. It is particularly advantageous if charging of the rechargeable battery occurs automatically when the medical device held by the stand is connected to an electrical grid.

Additionally or alternatively to the rechargeable battery, at least one primary battery can also be provided which serves as an energy storage device for supplying the drive unit with electrical energy. In addition, it is alternatively possible for the stand to be connected via a cable to an electrical network in order to supply the drive unit with energy.

The sensor unit preferably encompasses a speed sensor for ascertaining the speed of the displacement motion of the stand. The degree of assistance with which the caster is driven can in particular be speed-dependent. Alternatively, the drive unit can also drive the casters with a constant force irrespective of the speed ascertained with the aid of the speed sensor.

It is furthermore particularly advantageous if the control unit applies control to the drive unit in such a way that the latter assistively drives the at least one caster only when the actual speed of the displacement motion, ascertained with the aid of the motion sensor, is greater than a preset minimum speed and/or less than a preset maximum speed. The setting of a minimum speed that must be exceeded by the manual movement of the stand before the drive unit drives the caster in order to assist the displacement motion ensures that the displacement motion is assisted only in the context of what is in fact an intended displacement of the stand by an operator, so that displacement is made easier for the operator. In particular, this prevents the drive unit from driving the caster, and unintentionally moving the stand further, if the stand is accidentally bumped into.

The provision of a preset maximum speed ensures that the stand is not moved at too high a speed, and can thus be sufficiently decelerated again within a short braking distance so that collisions are avoided.

The driving of at least one caster in order to assist the displacement motion can occur both as an acceleration and as a deceleration of the rotary motion of the caster. The result is that on the one hand displacement of the stand itself is facilitated, and on the other hand deceleration of the stand is accelerated so that it can rapidly be brought to a standstill.

In particular when the stand is being moved over a downwardly sloping surface, assistive braking by the drive unit prevents the stand from accelerating. Collisions are thereby prevented.

It is furthermore advantageous if the control unit applies control to the drive unit in such a way that the latter drives the caster in such a way that the displacement motion becomes decelerated when the actual speed of the displacement motion, ascertained with the aid of the speed sensor, is greater than the maximum speed.

Additionally or alternatively to the speed sensor, the sensor unit can encompass a revolution counter for counting the revolutions of the caster, an acceleration sensor, a torque sensor, and/or a force sensor. The result thereby achieved is that the displacement motion is reliably detectable in simple fashion, and safe and reliable assistance of the displacement motion is thus achieved.

Thanks to the acceleration sensor it is possible in particular to ascertain whether a positive acceleration, i.e. an increase in speed, or a negative acceleration, i.e. a deceleration, of the stand is occurring. The control unit can accordingly apply control to the drive unit in such a way that both the (positive) acceleration and the deceleration in speed occur by way of corresponding driving of the assistively driven caster. A further result thereof is in particular that deceleration on slopes is achieved.

The casters of the stand are in particular movable between a displacement position in which they are arranged for displacement of the stand, and a support position in which they are arranged when the stand foot is placed on the floor. In the displacement position the casters are arranged in such a way that they project out of a support surface of the stand foot, and thus lift the stand foot off the floor so that the stand can easily be displaced. In the support position, conversely, the casters are received sufficiently far into recesses of the stand foot that they no longer project out of the support surface and thus do not contact the floor or at least do not lift up the stand, so that the stand is safely supported and cannot be unintentionally moved.

It is furthermore advantageous if a handle for manual displacement of the stand is arranged on the stand. The result of this is that the stand can easily be handled.

A manually actuable actuation element is, in particular, arranged on the handle, such that the control unit applies control to the drive unit so as to assistively drive the at least one caster only when the actuation element is, in particular, manually actuated. The result of this is to ensure that assistance of the displacement motion occurs only when actually desired by the operator. The actuation element is in particular a bail extending over the entire handle, so that the actuation element can be actuated in simple fashion irrespective of the position at which the operator grasps the handle, similarly to a lawnmower.

It is furthermore advantageous if a remote control system for controlling the drive unit and/or for controlling the displacement motion is provided. The drive unit and thus the displacement motion can be easily controlled in this manner. The remote control system either can be embodied in cable-based fashion or can occur wirelessly, for example via radio or infrared. For this the stand encompasses in particular a receiver, and the remote control a corresponding transmitter.

It is furthermore advantageous if a sensor for the detection of floor irregularities is provided, and if the control unit applies control to the drive unit in such a way that the drive unit assistively drives the at least one caster when said sensor detects a floor irregularity. Floor irregularities can be, in particular, doorsills that are recognized with the aid of the sensor. What is achieved thereby is that traveling over doorsills is made easier by the corresponding activation of the drive unit. The sensor for the detection of floor irregularities can be, in particular, a torque sensor.

It is moreover advantageous if the stand encompasses a marking sensor for recognizing floor markings. Such floor markings can be, in particular, markings for the identification of so-called "safety zones", i.e. zones in operating rooms within which devices must not be placed. The control unit applies control to the drive unit in such a way that the latter decelerates the stand when the marking sensor has detected a floor marking and the control unit has ascertained that the floor marking would be traveled over if the displacement motion continued. In particular, the control unit applies control to the drive unit in such a way that the latter decelerates the stand to a stop. This prevents floor markings from being traveled over, and thus in particular prevents unintentional displacement into safety zones. The marking sensor can be, in particular, an optical sensor.

BRIEF DESCRIPTION OF THE DRAWINGS

Further features and advantages of the invention are evident form the description that follows, which explains the invention in further detail with reference to exemplifying embodiments in conjunction with the attached Figures, in which:

FIG. 1 schematically depicts a stand for holding at least one medical device.

DETAILED DESCRIPTION OF THE INVENTION

FIG. 1 schematically depicts a stand 10 for holding medical devices W1 to W3. Medical device W1 is, in particular, a microscope, and medical devices W2 and W3 are auxiliary apparatuses, for example illumination systems. Alternatively, other medical devices W1 to W3, or only one medical device W1 to W3, or also no medical device W1 to W3, can be mounted on stand 10.

Stand 10 encompasses a stand foot 6 by means of which stand 10 is placed on the floor. Stand 10 further has a carrier unit 12 that can encompasses a first carrier 1 and a second carrier 2. The first carrier is mounted on stand foot 6 rotatably around a first axis S1. Second carrier 2 is in turn mounted on first carrier S1, rotatably around an axis S2. Further arranged articulatedly on second carrier S2 is a holding unit 5 on which medical devices W1 to W3 can in turn be mounted. Provided on carriers 1, 2 are respective slide mechanisms 3, 4 on which counterweights W4, W5 are provided for counterbalancing stand 10 so that medical devices W1 to W3 remain in the desired position that is established and do not of themselves move into other positions.

What is achieved by way of carrier unit 12 is that the position of medical devices W1 to W3 can be established in simple fashion, in particular that an optimal position for the surgical procedure can be selected.

Stand foot 6 comprises a support surface 14 by way of which it is placed on the floor. Stand foot 6 furthermore has multiple casters, one of which is labeled by way of example with the reference character 16. By way of casters 16, stand 10 can be displaced to different locations so that it can easily be conveyed to the particular utilization location or into a storage area.

Casters 16 can be adjusted in particular between a displacement position in which they project out of support surface 14, and a support position. In the support position they are received into recesses (not visible in FIG. 1) of stand foot 6 so that they do not project out of support surface 14. The support position is that position in which casters 16 are arranged when stand 10 is placed on the floor and is not intended to be displaced. Safe support of stand 10 is thus achieved in the support position, and easy displacement of stand 10 is enabled in the displacement position. Adjustment of casters 16 between the displacement position and support position can occur manually and/or automatically, for example with the aid of a drive unit.

Stand 10 furthermore has a drive unit 18 with the aid of which at least one of casters 16, preferably all casters 16, of stand foot 6 are drivable. Drive unit 18 encompasses in particular an electric motor, preferably a direct-current motor. An energy storage unit 19, in particular a rechargeable battery and/or a primary battery, is provided, with which the energy required by drive unit 18 is made available. The rechargeable battery is, in particular, charged when stand 10 is at a fixed location and in particular when medical devices W1 to W3 are being used. Alternatively, charging can be omitted when primary batteries are used.

Stand 10 furthermore has a control unit 20 for controlling drive unit 18, as well as a sensor unit 22 for ascertaining a displacement motion of stand 10. Control unit 20 applies control to the drive unit in such a way that the latter assistively drives casters 16 only when a displacement motion of stand 10 is detected via sensor unit 22. Drive unit 18 thus drives casters 16 not continuously, and also not by way of an actuation of a corresponding actuation element, but rather exclusively when stand 10 is being manually moved. What the drive unit instead accomplishes is merely to assist the displacement motion that is in any case already taking place, comparably to the assistance of a pedaling motion in the case of an electric bicycle, called a "pedelec."

Sensor unit 22 encompasses in particular a speed sensor with the aid of which the speed of the displacement motion is ascertained. In particular, a minimum speed and a maximum speed are preset in control unit 20. Control is applied to drive unit 18 in such a way that it assists the displacement motion only when the actual speed ascertained by sensor unit 22 is greater than the preset minimum speed and less than the preset maximum speed. Presetting of the minimum speed ensures that the displacement motion of the stand is assisted only when that motion is intentional. The maximum speed ensures that stand 10 is not moved at too high a speed, and can thus be brought to a stop within a comparatively short braking distance. In addition, presetting a maximum speed enables automatic deceleration of stand 10, thereby simplifying displacement over a downwardly sloping surface.

In general, "assistive driving" of the caster by the drive unit is understood as assistance of both a positive and a negative acceleration, i.e. assistance in increasing the speed, assistance in maintaining speed, and assistance in deceleration.

Sensor unit 22 can furthermore also encompass, for example, acceleration sensors, torque sensors, or force sensors.

In addition, a marking sensor for ascertaining floor markings, in particular a camera, can additionally be provided. Safety zones into which a medical device cannot ordinarily be conveyed are often marked in operating rooms using floor markings. Such floor markings are automatically detected with the aid of a marking sensor of this kind. Control unit 20 thereupon applies control to drive unit 18 in such a way that the latter automatically decelerates stand 10 so that stand 10 is not unintentionally conveyed over such a floor marking into a safety zone.

In addition, sensor unit 22 can also encompass a sensor for ascertaining floor irregularities, for example a torque sensor. This allows doorsills, in particular, to be recognized, in which context the control unit applies control to drive unit 18 in such a way that upon recognition of a doorsill, it assistively drives casters 16 so that stand 10 can easily be conveyed over the doorsill.

A handle 24 with which stand 10 can easily be moved manually is preferably arranged on stand 10. In a preferred embodiment, an actuation element embodied as bail 26 is arranged on said handle. Only when this bail 26 is actuated by the person displacing stand 10 does control unit 18 apply control to the drive unit, when the corresponding displacement motion is ascertained by way of sensor unit 22, in such a way that it assists the displacement motion. Without an actuation of bail 26, no assistance of the displacement motion by drive unit 18 occurs, so that in this case stand 10 can be displaced exclusively manually. What is achieved thereby is that the operator can easily decide at any time whether or not he or she wishes to be assisted in moving stand 10. Safe displacement of stand 10 can thereby be achieved.

Additionally or alternatively, a remote control system can also be provided with which the drive unit is actuable. In particular, the entire displacement motion can also be controlled with this remote control system.

Assistance of the displacement motion by way of drive unit 18 makes possible, in summary, simple and nevertheless safe displacement of stand 10. On the one hand, drive unit 18 allows the energy expenditure for displacing stand 10 to be decreased; on the other hand the entirely assistive effect, i.e. driving casters 16 only when a displacement motion already exists, contributes to ensuring that, unlike with a completely electric drive system, unintentional movement of stand 10 in an undesired direction is avoided or at least made more difficult.

The invention is not to be limited to the specific embodiments disclosed, and modifications and other embodiments are intended to be included within the scope of the invention.

PARTS LIST 1, 2 Carrier
3, 4 Slide mechanism
5 Holding unit

6 Stand foot
10 Stand
12 Carrier unit
14 Support surface
16 Caster
18 Drive unit
19 Energy storage unit
20 Control unit
22 Sensor unit
24 Handle
26 Bail
S1, S2 Axis
W1, W2, W3 Medical device
W4, W5 Counterweight

What is claimed is:

1. A stand for holding at least one medical device, comprising:
   a stand foot (6) for placing the stand (10) on a floor, the stand foot (6) including a plurality of casters (16) for displacement of the stand (10) relative to the floor;
   at least one sensor unit (22) configured to ascertain a displacement motion of the stand (10);
   a drive unit (18) configured to drive at least one of the casters (16) of the stand foot (6); and
   a control unit (20) configured to control the drive unit (18) such that the drive unit (18) assistively drives one or more of the plurality of casters (16) only when the sensor unit (22) detects a displacement motion of the stand (10); and
   a marking sensor configured to recognize a floor marking;
   wherein the control unit (20) is configured to control the drive unit (18) such that the drive unit (18) decelerates or stops the stand (10) when the marking sensor detects the floor marking and the control unit (20) ascertains that the floor marking would be traveled over if the displacement motion caused by a user continues; and
      wherein the sensor unit (22) includes a speed sensor configured to ascertain speed of the displacement motion;
      wherein the control unit (20) is configured to control the drive unit (18) such that the drive unit (18) drives the at least one caster (16) when the speed of the displacement motion, determined by the speed sensor, is greater than a preset minimum speed and/or less than a preset maximum speed; and
      wherein the control unit (20) is configured to control the drive unit (18) such that the drive unit (18) drives the at least one caster (16) to decelerate the stand (10) when the speed of the displacement motion, determined by the speed sensor, is greater than the maximum speed.

2. The stand (10) according to claim 1, further comprising a carrier unit (12), for mounting the at least one medical device (W1 to W3), the carrier unit (12) being articulatable on the stand foot (6).

3. The stand (10) according to claim 2, wherein the carrier unit (12) includes a holding unit (5) on which the at least one medical device (W1 to W3) is mounted.

4. The stand according to claim 3, wherein the at least one medical device (W1 to W3) is a microscope.

5. The stand (10) according to claim 1, wherein the drive unit (18) assistively drives at least two of the at least one caster (16) of the stand foot (6) when the sensor unit (22) detects a displacement motion.

6. The stand (10) according to claim 1, wherein the drive unit (18) assistively drives all of the at least one caster (16) of the stand foot (6) when the sensor unit (22) detects a displacement motion.

7. The stand (10) according to claim 1, wherein the drive unit includes (18) an electric motor.

8. The stand (10) according to claim 1, further comprising an energy storage unit (19) for storing electrical energy in order to supply the drive unit (18) with energy.

9. The stand (10) according to claim 8, wherein the energy storage unit (19) is a rechargeable battery and/or a primary battery.

10. The stand (10) according to claim 1, wherein the sensor unit (22) includes one or more of the following: a revolution counter for counting the revolutions of the caster (16), an acceleration sensor, a torque sensor, and a force sensor.

11. The stand (10) according to claim 1, wherein in a displacement position, for displacement of the stand (10), the casters (16) are arranged such that they project out of a support surface (14) of the stand foot (6); and
   wherein in a support position for placing the stand foot (6) on the floor, the casters (16) are received in receiving regions of the stand foot (6) such that they do not project out of the support surface (14).

12. The stand (10) according to claim 1, further comprising a handle (24) for manual displacement of the stand (10); and
   a manually actuable actuation element (26) arranged on the handle (24);
   wherein the control unit (20) is configured to control the drive unit (18) such that it assistively drives the at least one caster (16) only when the actuation element (26) is actuated.

13. The stand (10) according to claim 1, further comprising a remote control system for controlling the drive unit (18) and/or for controlling the displacement motion.

14. The stand (10) according to claim 1, further comprising a torque sensor configured to detect floor irregularities;
   wherein the control unit (20) is configured to control the drive unit (18) such that the drive unit (18) assistively drives the at least one caster (16) when the torque sensor detects a floor irregularity.

* * * * *